United States Patent [19]

Rounbehler et al.

[11] 4,194,884
[45] Mar. 25, 1980

[54] METHOD AND APPARATUS FOR AIR SAMPLING AND FILTRATION

[75] Inventors: David P. Rounbehler, Concord; David H. Fine, Framingham, both of Mass.

[73] Assignee: Thermo Electron Corporation, Waltham, Mass.

[21] Appl. No.: 963,626

[22] Filed: Nov. 24, 1978

[51] Int. Cl.$^2$ .................... G01N 31/06; G01N 31/08; G01N 31/12; G01N 33/00
[52] U.S. Cl. .............. 23/232 R; 23/232 C; 422/88; 422/89; 55/67; 55/387
[58] Field of Search .............. 23/232 R, 232 C; 422/83, 89; 55/67, 74; 73/23.1, 61.1 C; 252/457 R

[56] References Cited

U.S. PATENT DOCUMENTS

| | | | |
|---|---|---|---|
| 2,359,343 | 10/1944 | Winding | 252/457 X |
| 2,373,113 | 4/1945 | Francis | 422/88 |
| 2,393,625 | 1/1946 | Fitz | 252/457 |
| 3,069,897 | 12/1962 | Sanford | 55/67 |
| 3,506,732 | 4/1970 | Cowley et al. | 252/457 X |
| 3,650,279 | 3/1972 | Gansloser | 252/457 X |
| 3,791,522 | 2/1974 | Eisenbeiss et al. | 210/198 C |
| 3,888,972 | 6/1975 | Kiseler et al. | 252/449 X |
| 3,966,410 | 6/1976 | Jahnsen | 210/198 C |
| 3,996,002 | 12/1976 | Fine | 23/230 PC |
| 4,003,257 | 1/1977 | Fletcher et al. | 422/89 X |

OTHER PUBLICATIONS

Determination of N-Nitroso Pesticides in Air, Water & Soil, Fine et al., Sep. 2, 1976, 172 A.C.S. National Meeting.
Analysis of Air Pollutants Using Sampling Tubes & Gas Chromatography, Russel, Envir. Sci. & Tech. vol. 3, No. 13, 12–75.
Determination of Dimethylnitrosamine in Air & Water by Thermal Energy Analysis: Fine et al. Envir. Sci. & Tech. vol. 11, No. 6, 6/1977.

*Primary Examiner*—Michael S. Marcus
*Attorney, Agent, or Firm*—Herbert E. Messenger; James L. Neal

[57] ABSTRACT

Methods and apparatus for removing compounds from air to clean the air and for providing quantitative analysis of the content of particular organic compounds in the air. Apparatus is described having a separation zone packed with a magnesium silicate or calcium silicate material in the form of finely divided particles which are effective in trapping and holding substantially all of certain predetermined compounds present in air passed through the material. The silicate-packed separation zone may be employed as a highly efficient filter to purify air containing pollutants or contaminants. Also described are a method and apparatus for accurately determining the content of predetermined organic compounds in a sample of air using a collection tube containing a sorbent material such as dry, finely divided activated magnesium trisilicate. The method involves passing air through the sorbent material for a specified interval of time to trap the predetermined compounds, applying a solvent in the opposite direction to the flow of air to transfer all of selected compounds to a small quantity of solvent to form a solution, collecting the solution as it emerges from the material, and then analyzing the collected solution without concentrating it. One set of compounds of interest are highly carcinogenic N-nitroso compounds which may be present in air in minute quantities.

15 Claims, 6 Drawing Figures

METHOD AND APPARATUS FOR AIR SAMPLING AND FILTRATION

BACKGROUND OF THE INVENTION

This invention relates to air sampling and filtration systems and more particularly to methods and apparatus for removing compounds from air to clean the air and for providing quantitative analyses of the content of particular organic compounds in the air.

Devices are known for filtering air and for sampling air to identify types and levels of organic compounds present in the environment from a variety of sources such as the manufacture and use of chemicals, combustion of fuels, and others. Adsorbent materials are often employed in such devices to filter polluted air or trap measurable quantities of pollutants for analysis. However, while qualitative analyses of air are possible with these instruments and techniques, accurate quantitative analyses have proven difficult to achieve, particularly when the air to be analyzed contains complex organic compounds in low concentrations. One problem with use of adsorbent materials is that some adsorbents such as activated charcoal vary substantially in composition among manufacturers and between batches and also do not trap effectively certain low molecular weight compounds of interest. Moreover, after compounds are trapped, heat is commonly used to desorb the compounds from the adsorbent for analysis, and this frequently results in the formation of additional amounts of the compounds whose detection is sought or alteration of those trapped. Use of sophisticated and expensive materials such as gas chromatographic materials as adsorbents helps avoid variations in composition but not the heat desorption problem and may also involve "breakthrough" problems—i.e. during trapping certain compounds to be separated from the air gradually migrate through the gas chromatographic material in the direction of airflow and are lost from the collection device. Loss of a portion of the compounds introduces errors in a quantitative analysis and could also be a drawback to use of these materials in filtering apparatus such as gas masks or chemical hoods. Certain other adsorbents such as silica gel may have at least one of the above-mentioned drawbacks and in addition exhibit an affinity for moisture which degrades their trapping efficiency and renders them unsuitable for analysis or filtering of moist air.

Among the substances whose detection in air and/or removal therefrom are of importance are pesticide residues, compounds in vapors from explosives such as TNT, nitroglycerine, C4, and RDX, industrial pollutants such as nitrobenzene, vinyl chloride, acetonitrile, and acrylonitrile, organic compounds present in automobile and truck emissions and in cigarette smoke, and others. Of particular interest in the present invention, in addition to these compounds, are N-nitroso compounds or N-nitrosamines, each of which have the general formula

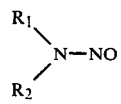

where $R_1$ and $R_2$ are the same or different organic radicals including those radicals which together with the depicted N-NO molecular bond constitute a nitrogen heterocyclic radical. These N-nitroso compounds include as a group several which are known to be potent carcinogens, and dosages of a few parts per million of these N-nitrosamines have produced cancers in animals. The high carcinogenity of these compounds when inhaled or ingested has caused much concern regarding their occurrence in certain materials and in the environment.

In the continuing search for the presence of these N-nitroso compounds and their possible role in causing cancer in humans, considerable interest has developed in monitoring air such as that in or near factories and cities where volatile N-nitroso compounds have been found and non-volatile N-nitroso compounds may also occur under certain conditions. However, in contrast to foods and chemicals, samples of which have readily been obtained for measurement of the content of N-nitroso compounds, accurate collection and analysis of samples from atmospheric environments is considerably more difficult as mentioned above in the general discussion of air sampling and filtering. This is true particularly if rapid collection and analysis are desired to monitor air whose quality is susceptible to change and/or to monitor air by means of devices sufficiently portable to be worn by personnel. It is important, for example, that the technique and apparatus used to filter or test air for the presence of N-nitrosamines or other organic compounds, whether or not part of a portable system, permit trapping and retention of substantially all of the predetermined compounds in the air sampled, and quite desirable that the system of which they are part provide accurate and rapid analysis of the compounds extracted from the air.

One prior method of detecting N-nitroso compounds in air is to bubble air through a solution of KOH (potassium hydroxide), extract the contents of the trap using a solvent, dry and then concentrate the extract, and then analyze the extracted sample for the presence of N-nitroso compounds. One major disadvantage of this method is that collection efficiency is low for certain N-nitroso compounds of interest such as N-nitrosodipropylamine, over 80 percent of which may pass through the bubble trap. Also, this method requires drying and concentration of the extract as by evaporation, which necessitates precise measurements and controls, is time consuming, and may introduce errors in the analysis. The collection apparatus utilized in this technique is also too cumbersome for use in a personnel monitor and requires caustic solutions whose preparation, use, and disposal present hazards to personnel and to equipment such as air pumps.

Another method which has been used to monitor air for N-nitroso compounds is to draw air through cartridges containing Tenax GC material, a gas chromatographic material available from Applied Science Laboratories, Inc., State College, Pa., desorb the trapped materials using heat, then analyze the desorbed materials as by capillary gas-liquid chromatography followed by low-resolution mass spectrometry. However, not only is Tenax GC material quite expensive but if desorption by heat is used after collection inaccuracies can result since the thermal desorption may produce N-nitroso compounds from precursors such as amines and compounds containing nitrogen and/or oxygen present on the cartridge or may cause decomposition of some of the N-nitroso compounds trapped. Another deficiency of Tenax GC material is that it may not retain all of the N-nitroso compounds in the air pumped through the cartridge. The collection efficiency has been found in tests to be different for different N-nitroso compounds and after a certain volume of air has been drawn through the cartridge, further monitoring results in the "breakthrough" and loss of certain N-nitroso compounds from the cartridge. The breakthrough volume of air is different for different N-nitroso compounds, being generally lowest for the smaller N-nitroso compounds (such as N-nitrosodimethylamine) which are of maximum interest.

Accordingly, it is a general object of this invention to provide improved methods and apparatus for removing organic compounds from air.

It is a more particular object of the invention to provide a method and apparatus for determining the content of predetermined organic compounds in a sample of air.

It is another object of the invention to provide improved apparatus for filtering air to clean the air of particular compounds.

It is an object of the invention to provide a method for determining the content of predetermined organic compounds in a sample of air wherein the compounds may be trapped and then collected in a volume of solution sufficiently small so as to not require concentration of the solution during the determination.

It is also an object of the invention to provide apparatus for collecting organic compounds from air which is compact, inexpensive, portable, and simple to use.

It is a particular object of the invention to provide as improved method and apparatus for determining the content of N-nitroso compounds in air.

It is another object of the invention to provide apparatus for collecting N-nitroso compounds from air which will separate substantially all of the N-nitroso compounds from air directed through the apparatus and hold them without loss, then release substantially all of the N-nitroso compounds into a liquid solvent to form a solution analyzable for the total N-nitroso compound content without concentration of the solution.

SUMMARY OF THE INVENTION

Methods and apparatus are provided for removing organic compounds from air and for determining the content of predetermined compounds in a sample of air. According to the invention collection apparatus is supplied having a separation zone between an inlet and an outlet. The separation zone is packed with a solid sorbent material such as a magnesium silicate or calcium silicate material in the form of finely divided particles pervious to the flow of air therethrough but very effective in trapping and holding organic compounds such as industrial pollutants, vapors from explosives, and pesticide residues. The collection apparatus may be employed as a filter to clean air which is directed through the sorbent material or used in conjunction with known analytical techniques such as mass spectroscopy, chromatography, and selective pyrolysis to provide accurate quantitative analysis of air samples. Certain preferred embodiments of the invention cover a method and apparatus for determining the content of N-nitroso compounds in a sample of air including the steps of passing a specified volume of air through a collection tube containing a finely divided sorbent material such as activated magnesium trisilicate, applying a liquid solvent to the material in a direction opposite to the flow of air to remove all of the N-nitroso compounds by forming a solution of solvent and N-nitroso compounds, collecting the solution as it emerges from the tube, and analyzing the solution for N-nitroso compound content by pyrolysis followed by measurement of the amount of nitric oxide liberated. An important feature of the air-sampling systems of the invention, in addition to the simple, inexpensive, rapid sampling they provide, is the transferability of substantially all of selected compounds from the sorbent material into a very small volume of solution, which eliminates a requirement to concentrate the solution following collection and prior to analysis for the presence and amounts of selected organic compounds.

DETAILED DESCRIPTION OF PREFERRED EMBODIMENTS OF THE INVENTION

Figure 1:
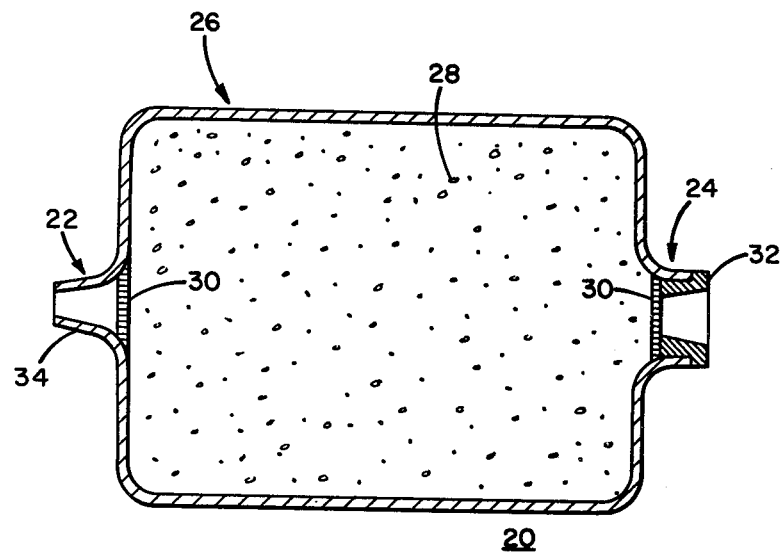
FIG. 1 is a sectional view of a collection tube suitable for use in certain preferred embodiments of the invention.

FIG. 1 shows a sectional view of a collection tube 20 which may be used to separate predetermined organic compounds from air. Among the many organic compounds which may be filtered and/or removed for analysis are compounds in vapors from explosives such as nitroglycerine, pollutants such as vinyl chloride, and N-nitroso compounds such as N-nitrosodimethylamine, -diethylamine, -dipropylamine, -morphorline, -pyrolidine, -diethanolamine, -piperidine, -dibutylamine, -dihexylamine, -nornicotine, and -methylvinylamine. Tube 20 may be employed as a filter to clean these or other unwanted substances from air but is more particularly adapted for use as part of a sampling system for quantitative analysis of specified compounds in air. In the description to follow embodiments of the invention directed to the latter use are set forth in considerable detail; however it should be understood that the essential principles of collection are applicable to air filtration and that collection tube 20 may be readily modified for use in such devices as gas masks, hoods for chemical apparatus, and various other air-conditioning apparatus.

As shown in FIG. 1, collection tube 20 is a thin-walled tube comprising an inlet 22, an outlet 24, and a separation zone 26 between inlet 22 and outlet 24. Separation zone 26 is preferably cylindrical and considerably larger in diameter than inlet 22 and outlet 24 and contains finely divided particles of a solid sorbent material 28 forming a bed which is pervious to the flow of air therethrough but uniquely suited to separate organic compounds from air and retain them in collection tube 20 as will be explained in more detail hereinafter. The material 28 is held within separation zone 26 by a porous glass fiber disk 30 or other suitable retention means located at each end of separation zone 26.

Figure 2:
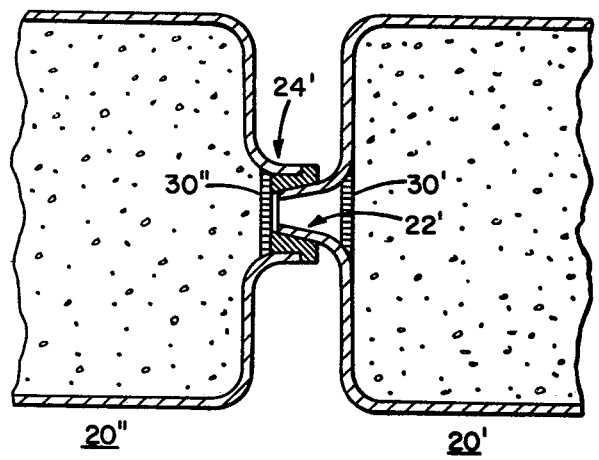
FIG. 2 shows portions of two collection tubes similar to the tube of FIG. 1 and illustrating their connection in series.

Inlet 22 and outlet 24 accommodate the flow of air through collection tube 20 during trapping of N-nitrosamines, carbonaceous products of the combustion of fuels, and other organic compounds, and outlet 24 is readily connectable to a hose 31 (FIG. 5) of an air pump (not shown) used to draw air successively through inlet 22, separation zone 26, and outlet 24 of tube 20. In the preferred embodiment of the invention shown in FIG. 1, outlet 24 includes a ring-shaped adapter 32 at the outlet end of tube 20 to permit the insertion thereinto of the tip of a syringe containing a liquid solvent used to remove or back-flush selected compounds from tube 20 following trapping thereof. The inner and outer diameters of wall 34 of inlet 22 decrease in a direction away from separation zone 26 (opposite to airflow direction) to help direct the flow of solvent plus desorbed compounds out of tube 20 for subsequent collection thereof and to permit series connection of two or more collection tubes if desired. A series arrangement of two tubes, for example, as shown in FIG. 2 where inlet 22' fits tightly into the outlet 24'' of an upstream tube 20'', could be used to demonstrate that collection tube 20' is adequate in a particular collection situation to prevent "breakthrough" or loss of compounds to be trapped and analyzed, or to trap compounds should breakthrough occur after extremely long periods of sampling and/or sampling of large volumes of air (no breakthrough has yet been found to occur, and tests have confirmed no breakthrough after 16 hours of trapping at a continuous airflow rate of 2 liters per minute).

An important feature of collection tube 20 is the sorbent material 28 provided in separation zone 26, which satisfies several criteria for accurate monitoring of air for organic compounds. First, material 28 permits trapping of substantially all (greater than 95 percent) of predetermined compounds present in the air passed through tube 20 and holds these compounds without loss thereof during the entire monitoring interval, which may range from a few minutes to several hours. Material 28 also does not react chemically with the compounds trapped thereby to form different compounds and does not combine with precursors to form the compounds whose content is to be determined. Further, material 28, when selected with appropriate particle sizes and packed in a bed of suitable thickness within separation zone 26, accommodates the passage of air therethrough during sampling at a flow rate sufficiently high to permit a desired volume of air to be sampled quickly. Rapid sampling is essential for monitoring air whose composition is subject to change such as in a factory whose processes and output may vary rapidly, or to permit several different samples to be taken in a given area during a prescribed time —e.g. by a mobile unit. And finally, material 28, in addition to separating and holding substantially all of the compounds of interest in a large volume of air without "breakthrough" and loss from collection tube 20, readily releases selected compounds into a solvent passed through tube 20 to permit subsequent analysis of these compounds.

The materials preferred for use as sorbents within separation zone 26 are magnesium or calcium silicates or mixtures thereof in the form of finely divided particles of 10-200 mesh size, preferably dry and of 60-80 mesh size. The silicates may be prepared by cleaning, drying, and crushing naturally occurring silicates such as magnesium orthosilicate ($Mg_2SiO_4$), calcium orthosilicate ($Ca_2SiO_4$), magnesium metasilicate ($MgSiO_3$), or serpentine ($Mg_3Si_2O_7.2H_2O$), or by co-precipitating soluble compounds such as magnesium sulfate and sodium silicate in water—e.g. to form magnesium trisilicate ($Mg_2Si_3O_8$), then drying and crushing the precipitate. One magnesium silicate material which has been tested and found to trap and hold N-nitroso compounds very effectively when used in either a dry state or wet with an acid or base is manufactured by the Floridin Company of Warren, Pa. and sold under the tradename Florisil by Fisher Scientific Company of Fair Lawn, N.J. Magnesium silicate materials and methods for their preparation are described in U.S. Pat. No. 2,393,625, issued Jan. 29, 1946 to O. F. Simons and assigned to Floridin Company.

The above-described materials, unlike some sorbents, are inexpensive and therefore the capacity for re-use of the magnesium or calcium silicate materials is not an important consideration in collection and analysis of air samples, particularly in typical applications where a relatively small volume of material is used in each collection tube.

For those embodiments of the invention wherein air filtering is contemplated, and re-use is desired, the silicate materials may periodically be cleansed of trapped compounds by passing solvents through the silicate material or by heating the materials at temperatures up to 1500° C. to desorb the trapped compounds.

Figure 3:
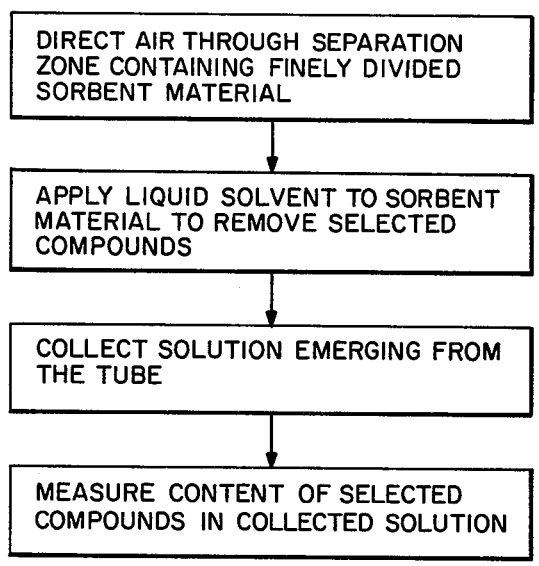
FIG. 3 is a block diagram showing the steps employed in carrying out a method for determining the content of certain organic compounds in air according to the invention.
Figure 5:
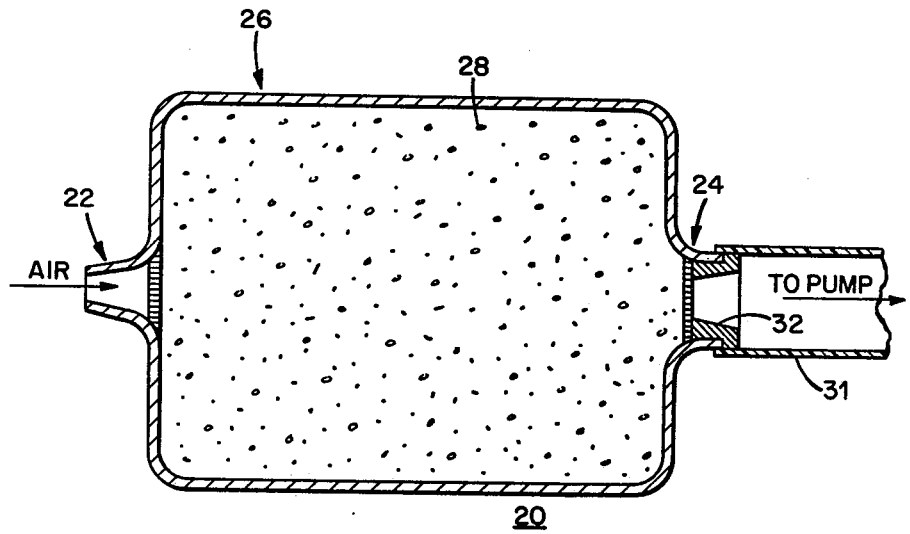
FIGS. 5 and 6 are sectional views of the collection tube of FIG. 1 illustrating, respectively, operation during collection of predetermined organic compounds from air and operation during removal of selected compounds from the tube by application of a liquid solvent.

FIG. 3 shows in block diagram form a method of detecting predetermined compounds in which collection tube 20 may be employed. According to this embodiment of the invention, after outlet 24 of collection tube 20 is connected to a pump, air is directed successively through inlet 22, separation zone 26, and outlet 24 of tube 20 as shown in FIG. 5 for a time sufficient to sample a predetermined volume of air. During the sampling interval the predetermined compounds, if present in the air, are separated therefrom and held tightly by sorbent material 28 in separation zone 26. After the prescribed volume of air has been monitored, the pump is disconnected and a solvent is applied, preferably at outlet 24 of tube 20, to separate the selected compounds such as N-nitrosamines from material 28. The solvent and substantially all of the selected compounds previously trapped on material 28 form a solution which emerges from tube 20 and is collected, then the collected solution is analyzed for content of the selected compounds by known methods such as techniques involving mass spectrometry or pyrolysis which are described in greater detail hereinafter.

The solvent employed to remove selected compounds from sorbent material 28 is determined in part according to the polarity of compounds to be removed, by the requirement that chemical reactions not occur between the solvent and either sorbent material 28 or compounds trapped thereby to form or alter any compounds whose detection is sought, and by the nature of the analytical techniques to be applied to measure the content of selected compounds removed from collection tube 20. (For example a polar solvent such as water removes polar N-nitroso compounds from sorbent material 28 but is not preferred since a further separation of the N-nitroso compounds from the water would typically be required prior to quantitative analysis of the N-nitroso compounds). Also, different solvents may be applied in succession to elute a series of selected compounds from collection tube 20. Suitable solvents for removing substantially all of, for example, the N-nitroso compounds trapped within collection tube 20 are dichloromethane (DCM), methanol, acetone, ether, or mixtures thereof. Examples of specific mixtures which may be used are, by volume, 80 percent DCM and 20 percent methanol; 60 percent acetone and 40 percent DCM, and 50 percent DCM and 50 percent methanol, a mixture currently preferred for removal of N-nitroso compounds since its polarity results in the desired selectivity—i.e., all N-nitroso compounds are removed while certain compounds not of interest are left trapped within collection tube 20.

To remove selected compounds trapped by sorbent material 28, the appropriate solvent is applied to tube 20, preferably in a manner such that solvent flows through separation zone 26 in the opposite direction from the flow of air therethrough—i.e., by back-flushing. A preferred technique illustrated in FIG. 6 involves attachment of a hollow needle 38 to inlet 22 of collection tube 20 and insertion of the tip of a syringe 40 containing a suitable solvent into outlet 24. As solvent is applied to separation zone 26, needle 38 imposes a slight back pressure on the flow of solvent so that it fills substantially all of separation zone 26 and solvent contacts all of material 28 before it is discharged at the tip of needle 38. (In the absence of needle 38, the solvent might tend to "channel" and not wet all of material 28, thus failing to remove some of the selected compounds unless large volumes of solvent were used.) The leading portion of solvent—i.e., that which first emerges from needle 38—removes the selected compounds, if present, forms a solution therewith, and emerges from the tip of needle 38. The solution is collected and is then available for analysis for content of the selected compounds.

Tests of the above-described back-flushing technique on elution of N-nitroso compounds have shown that it permits removal of substantially all of the N-nitroso compounds from tube 20 with a very small volume of solvent. For example, virtually all of the N-nitroso compounds contained in a tube with a separation zone 20 mm long and 15 mm in diameter filled with Florisil material of 60-100 mesh size and which sampled 360 liters of air containing a known quantity of N-nitrosodimethylamine, N-nitroso-diethylamine, N-nitrosodipropylamine, and N-nitroso-morpholine were detected in the first milliliter of solution collected after back-flushing the tube with a mixture of 80 percent DCM and 20 percent methanol. It is believed that the reason back-flushing is highly effective in removing compounds such as N-nitroso compounds whereas flushing in the forward, or airflow, direction is less effective and hence necessitates the use of considerably more solvent is that during sampling most of the compounds are trapped and held in the first few millimeters of material of separation zone 26 contacted by the air. Thus during back-flushing the compounds need to be moved only a short distance by the solvent to pass out of separation zone 26, while if forward flushing is employed the compounds must be moved through a considerably greater portion of the separation zone, increasing the liklihood of their reattachment to sorbent material 28 in separation zone 26. The removal of substantially all the N-nitrosoamines or other compounds from collection tube 20 in a very small volume of solution provides an important advantage over prior techniques since it renders unnecessary the subsequent distillation or evaporation required in prior methods in order to obtain the selected compounds in concentrations sufficiently high for analysis. Such evaporations would be time-consuming, require precise measurements, and also demand careful controls to avoid formation of artifacts or loss of compounds to be analyzed.

After elution of selected compounds from tube 20 the solution is analyzed according to known techniques. One preferred method for measuring the N-nitroso compound content of a sample is set forth in U.S. Pat. No. 3,996,002 "Method and Apparatus For Measuring the N-nitroso Compound Content of a Sample" issued to D. H. Fine, which disclosure is incorporated herein by reference. In this method a liquid sample containing N-nitroso compounds is non-catalytically pyrolyzed at a temperature in the range 300° C.–500° C. to break the N-NO bond and liberate gaseous nitric oxide without breaking substantial numbers of other molecular bonds, then the amount of nitric oxide liberated is measured as by reacting the nitric oxide with ozone and sensing the intensity of the resulting chemiluminescent reaction. Since the presence of nitrates and nitrites trapped by and eluted from tube 20 might impair the accuracy of detection of N-nitroso compounds, this measurement method preferably also includes a step prior to pyrolysis of the N-nitroso compounds wherein the N-nitroso compounds are chromatographically separated from each other and from any nitrate or nitrite compounds present in the sample. Suitable apparatus for performing the above-described analytical techniques is also described in U.S. Pat. No. 3,996,002 and is available as a TEA-Gas Chromatograph (TEA-GC) or TEA-High Pressure Liquid Chromatograph (TEA-HPLC) from Thermo Electron Corporation, Waltham, Massachusetts.

Another method which may be used to measure the N-nitroso compound content of the sample extracted from collection tube 20 involves flash heating the collected solution, applying the resulting vapor to a gas chromatograph, converting the N-nitroso compounds in the effluent from the chromatograph to ammonia in the presence of hydrogen, dissolving the ammonia in water, detecting the ammonia content by measuring the change in conductivity, and confirming the presence of N-nitroso compounds by mass spectroscopy. This method is less preferred than that set forth in U.S. Pat. No. 3,996,002 since formation of N-nitroso compounds from precursors such as $C-NO_2$ compounds and amines is likely during flash heating and since identification of unknown compounds cannot readily be accomplished.

A third technique which may be used for measuring the content of organic compounds extracted from tube 20 is to introduce at least part of the solution into a gas chromatograph which is interfaced to a mass spectrometer and to identify the organic compounds by mass spectrometry.

Figure 6:
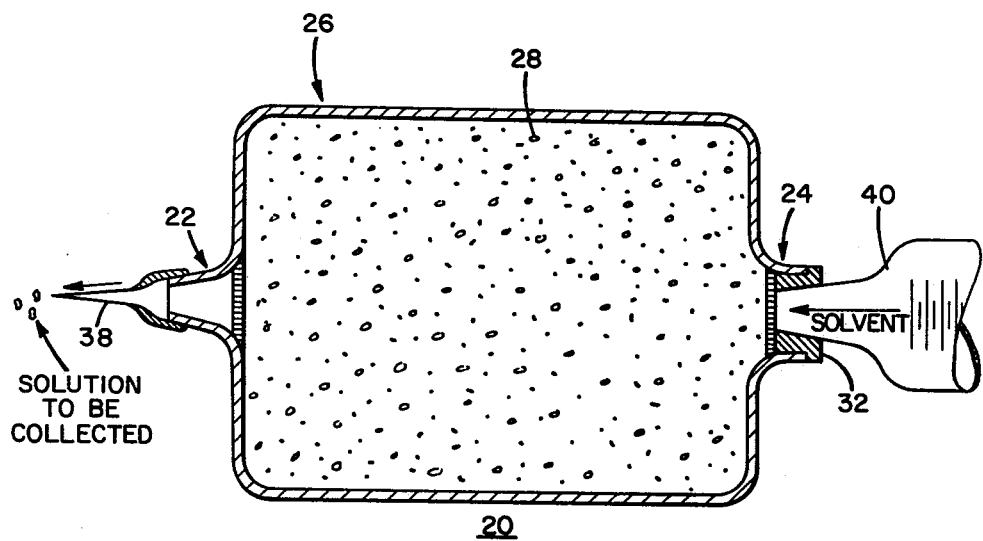

An example of a test conducted using the apparatus shown in FIGS. 1, 5 and 6 and the method of the invention shown in FIG. 4 will now be given. A plastic collection tube was provided with dry Florisil material of 60-100 mesh size in a separation zone approximately 20 mm. in length and 15 mm. in diameter. Twenty-five microliters of dichloromethane containing five micrograms each of N-nitroso-dimethylamine, N-nitroso-diethylamine, N-nitroso-dipropylamine, and N-nitroso-morpholine were placed in a flask and air was drawn over this mixture and through the collection tube at a rate of two liters per minute for three hours, which resulted in removal of all of mixture from the flask. The pump was disconnected and the tube back-flushed using a syringe containing a solvent consisting of 80 percent dichloromethane and 20 percent methanol by volume. Two half-milliliter samples of liquid which included the first, or leading, portion of solvent to emerge from the tube were collected, 2 percent by volume of each portion was introduced into a gas chromatograph to separate the N-nitroso compounds from each other, the effluents from the chromatograph were pyrolyzed to selectively liberate NO gas, and then the NO gas was measured to determine the amount of N-nitroso compounds present. Results showed that substantially 100 percent of the N-nitroso compounds present in the air passed through the tube were trapped and held in the separation zone, that about 90 percent of the N-nitroso compounds were contained in the first half milliliter of liquid which emerged from the tube, and substantially 100 percent of the N-nitroso compounds were contained in the first milliliter of liquid which emerged from the tube.

In a related test conducted to determine whether the magnesium silicate material exhibited "breakthrough" or loss of N-nitroso compounds after several hours of air sampling, no breakthrough was observed even after drawing air containing N-nitroso-dimethylamine, N-nitroso-diethylamine, N-nitrosodipropylamine, and N-nitroso-morpholine through the collection tube for sixteen hours at a rate of two liters per minute.

An example of an application of the invention wherein collection tube 20 may be used to monitor industrial pollutants is as follows. Fill a 20 mm by 15 mm separation zone of a tube similar to that shown in FIG. 1 with dry calcium trisilicate ($Ca_2Si_3O_8$) material of 60–80 mesh particle size. Draw air which may contain butadiene, styrene, and ethylene diamine through the tube at ten liters per minute for ten minutes and back flush with a solvent consisting of 50 percent dichloromethane and 50 percent methanol by volume. Collect the first milliliter of solution which emerges from the inlet of tube 20 and vaporize and inject at least a portion of the solution into a gas chromatograph interfaced to a mass spectrometer. Analyze the output of the mass spectrometer for the content of butadiene, styrene, and ethylene diamine.

It will be readily understood that the collection apparatus of the invention provides a simple inexpensive means for removing organic compounds from the air either to clean the air or for quantitative analysis of the content of predetermined compounds in the air. The collection tube, when used as an integral part of the above-described method for analyzing air, offers substantial reductions in the time and effort required to determine concentration of substances such as N-nitroso compounds whose presence in the air in even minute quantities is of growing concern.

The compact size of the collection tube readily permits incorporation of this device into a system having a small battery-operated pump and capable of being worn by selected personnel in a factory or other site for monitoring air substantially the same as that inhaled. It also facilitates shipment of the tube to a central laboratory for analysis of the compounds trapped in remote locations. Because the sorbent material employed in the tube traps and retains predetermined organic compounds very efficiently, a relatively thin separation zone may be utilized and air may be drawn through the tube at flow rates up to 40 liters per minute, permitting meaningful samples to be taken in short time intervals such as five minutes. Since only a small amount of the proper type of solvent is required to remove all of selected compounds from the tube, concentration of the solution of solvent and eluted compounds after its emergence from the tube is unnecessary, permitting a substantial reduction in time and cost of an analysis and reducing the risk of artifact formation or loss of the collected compounds.

Thus accurate collection and analysis of air for N-nitrosamines or other compounds may be accomplished in ten minutes or less, for example to determine which of several machines or processes that run at different times or in different areas contribute specific types and amounts of N-nitroso compounds to an environment. Further, in view of the ability of the disclosed collection tubes to trap and retain N-nitroso compounds without loss while sampling a large volume of air, the invention readily permits accurate sampling over extended periods of time, which is valuable, for example, in obtaining average daily levels of these compounds present in the air.

While there have been shown and described what are considered preferred embodiments of the invention, it will be apparent to those skilled in the art that various modifications may be made therein without departing from its essential nature. It is intended by the appended claims to claim all modifications which fall within the true spirit and scope of the invention.

What is claimed is:

1. A method of determining the content of predetermined organic compounds in a sample of air comprising in sequence the steps of:
    directing a predetermined volume of air through a separation zone containing finely divided particles of a material selected from the group consisting of magnesium silicates, calcium silicates, and mixtures thereof for removing from air and holding the predetermined compounds, said zone being pervious to the flow of air therethrough;
    applying a liquid solvent for selected compounds to said material, said solvent effecting the transfer of substantially all of said selected compounds held by said silicate material to the leading portion of said solvent to form a solution therewith;
    collecting said solution after emergence thereof from said separation zone; and
    measuring the content of said selected compounds in at least a portion of said collected solution.

2. The method of claim 1 wherein said material is a dry activated magnesium silicate having a particle size of 40–100 mesh and substantially all of the predetermined organic compounds are removed from the air directed through said separation zone.

3. The method of claim 1 wherein said step of applying the liquid solvent to said silicate material comprises passing said liquid solvent through said separation zone in the opposite direction from the flow of said sample of air to back-flush the selected compounds from said zone.

4. The method of claim 1 wherein the selected compounds comprise N-nitroso compounds having the general formula

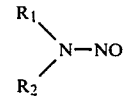

UNITED STATES PATENT AND TRADEMARK OFFICE
CERTIFICATE OF CORRECTION

Figure 4:
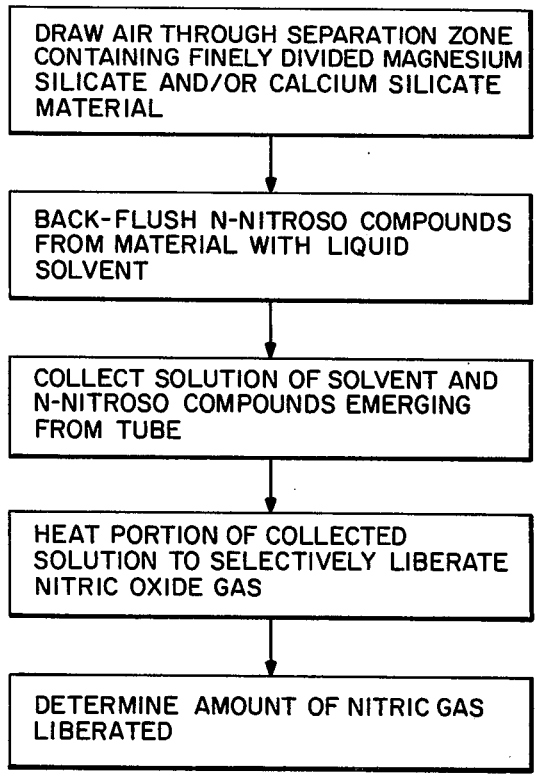
FIG. 4 is a block diagram showing the steps employed in a preferred method of the invention for determining the content of N-nitroso compounds in a sample of air.

PATENT NO. : 4,194,884
DATED : March 25, 1980
INVENTOR(S) : David P. Rounbehler, David H. Fine It is certified that error appears in the above-identified patent and that said Letters Patent are hereby corrected as shown below:

In the title page and in sheet 2 of the drawings, the word "oxide" should be added to the lowermost block of the Fig. 4 block diagram so that the block reads:

-- DETERMINE AMOUNT OF NITRIC OXIDE GAS LIBERATED --

In the specification at column 1, line 67, after the word "the" add - non-nitroso N of the -.

In claim 4 at column 11, line 2, after the word "the", add - non-nitroso N of the -.

In claim 6 at column 11, line 24, after the word "wherein", delete "$R_1$, $R_2$" and substitute therefor - $R_1$ and $R_2$ -.

In claim 6 at column 11, line 25, after the word "the", add - non-nitroso N of the -.

Signed and Sealed this

Twenty-fourth Day of June 1980

[SEAL]

Attest:

SIDNEY A. DIAMOND

*Attesting Officer*  *Commissioner of Patents and Trademarks*